United States Patent [19]

Hollman

[11] Patent Number: 4,688,517
[45] Date of Patent: Aug. 25, 1987

[54] PROCESSING APPARATUS

[75] Inventor: William Hollman, Tucson, Ariz.

[73] Assignee: Australian Biomedical Corporation Limited, Australia

[21] Appl. No.: 768,339

[22] Filed: Aug. 22, 1985

[30] Foreign Application Priority Data

Aug. 23, 1984 [AU] Australia .............................. PG6725

[51] Int. Cl.$^4$ .......................... B05C 3/05; B05C 3/09
[52] U.S. Cl. .................... 118/421; 118/697; 118/704; 118/425
[58] Field of Search ............... 118/425, 704, 421, 697; 422/64; 134/121, 137, 140, 142, 150

[56] References Cited

U.S. PATENT DOCUMENTS 3,809,008  5/1974  Takahashi ....................... 118/425 X
4,447,395  5/1984  Englar et al. ..................... 422/64 X

FOREIGN PATENT DOCUMENTS 369944  6/1923  U.S.S.R. .............................. 118/425

Primary Examiner—Evan K. Lawrence
Attorney, Agent, or Firm—Stevens, Davis, Miller & Mosher

[57] ABSTRACT

Apparatus for processing samples, such as tissue samples, including a rotatable table which carries either the samples or solutions in which the samples are to be immersed. The table is rotatable between a series of sample processing stations and is also arranged for axial movement between positions at which a sample is and is not respectively immersed in a solution. A single reversible motor is operable to both rotate the table and cause axial movement thereof. The motor drives a spindle having a double helix and also drives the table through a one way clutch arranged so that in one mode of operation the motor rotates both the spindle and the table and in another mode it rotates the spindle only. In the latter case the table is caused to move up and down the spindle as a result of cooperation between a follower and the helix tracks of the spindle.

13 Claims, 7 Drawing Figures

PROCESSING APPARATUS

This invention relates to apparatus for processing samples and is particularly but not exclusively concerned with such apparatus as used to process tissue samples. By way of example, such apparatus is used in hospital pathology departments and laboratories to prepare samples for microscopic examination - e.g., examination through an electron microscope. Example samples prepared in that way are skin tissues or tissues from organs such a the liver, kidney, or heart. It will be convenient to hereinafter describe the invention with particular reference to tissue processing apparatus, but it is to be understood that the invention has other applications. In that regard, the apparatus according to the invention can be used for biological and non-biological purposes.

Apparatus of the foregoing kind is generally of complex and expensive construction. Indeed, the cost of satisfactory apparatus is so prohibitive that some organizations continue to manually process tissue samples and that is a labourious and time consuming operation.

It is an object of the present invention to provide relatively simple apparatus which enables convenient processing of a sample or a plurality of samples. It is a further object of the invention in a particular form to provide such apparatus which enables convenient processing of tissue samples. It is yet another object of the invention to provide such apparatus which requires only one drive motor to perform a plurality of functions.

According to the present invention, there is provided a sample processing apparatus including, a carousel mounted for rotation and for back and forth movement in the direction of the axis of said rotation, and control mechanism operable to cause said rotation and said axial movement of the carousel, said control mechanism including, a drive motor which operates both in a forward mode and a reverse mode and transmission means which interconnects said carousel and said drive motor, and said transmission means is responsive to operation of said motor in one said mode to cause said carousel rotation and is responsive to operation of said motor in the other said mode to cause said carousel axial movement.

In a preferred arrangement the carousel is mounted on an upstanding rotatable spindle having a two way helix formed therealong and a follower is connected to the carousel so as to engage with the helix. That engagement is such that the carousel is caused to move axially on or along the spindle when there is relative rotation between the spindle and carousel. It is also preferred that the drive connection between the motor and spindle includes a one way clutch which operates to allow the spindle to rotate relative to the carousel in one direction and to prevent such relative rotation in the opposite direction.

The essential features of the invention and further optional features, are described in the following passages of the specification which refer to the accompanying drawings. The drawings however, are merely illustrative of how the invention might be put into effect, so that the specific form and arrangement of the features (whether they be essential or optional features) shown is not to be understood as limiting on the invention.

Apparatus according to the invention includes a rotatable carousel or table which carries either the sample or samples or at least one container in which the or each sample is to be immersed. In the particular form shown in the accompanying drawings the rotatable table 1 is adapted to carry a plurality of containers or vials 2, but as indicated above other arrangements could be adopted. The apparatus further includes a single reversible motor 3 which is operable to cause the table 1 to rotate during one part of the sequence of operations and to move axially during another part of that sequence.

Figure 2:
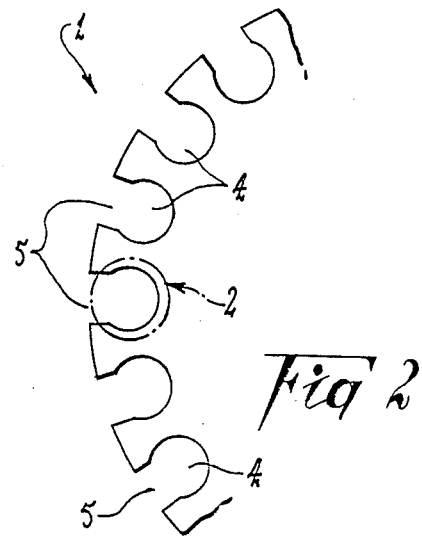
FIG. 2 is a view taken along line II—II of FIG. 1.
Figure 3:
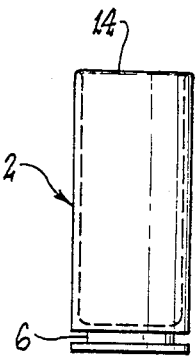
FIG. 3 is a side elevational view of a container or vias as used with apparatus according to the invention.

The example arrangement shown in the drawings is particularly suited for processing tissue samples, and in that arrangement the rotatable table is circular and is adapted to carry a plurality of open-topped containers or vials 2. The vials 2 are arranged in a circle and may be attached to or mounted on the table 1 in any suitable fashion. In the arrangement particularly shown however, the table 1 includes a plurality of mounting stations in the form of circular openings 4 each of which is connected to the table periphery through a passage 5 which has a width less than the diameter of the opening 4 (FIG. 2). As shown in FIG. 3, each vial 2 has a neck portion 6 of reduced diameter adjacent its lower end and that neck portion 6 has a diameter such as to neatly fit within an opening 4. The passage 5 however, is narrower than that diameter and the vial 2 and/or the table 1 has sufficient resilience or flexibility to allow the neck portion 6 to be pushed through the passage 5 for snap engagement within the opening 4. Other arrangements could be adopted to achieve the same result.

If desired, the table 1 may be arranged to carry two or more concentrical circles of vials 2. The table 1 is preferably mounted on an an upstanding column 7 as hereinafter described in detail. In other arrangements however, the column 7 may be arranged at an angle or it may extend horizontal rather than vertical as shown.

A sample supporting member 8 is arranged to overlie the table 1 and is adapted to carry at least one sample so that it may be immersed as required in a vial 2. The supporting member 8 as shown is in the form of a plate-like cover which is mounted so as to be restrained against movement in any direction. Nevertheless, means may be provided whereby the member 8 may be detached from the rest of the apparatus to allow, for example, removal and/or attachment of tissue samples. Furthermore, in other arrangements the member 8 could be in the form of an arm which overhangs the table 1 and such an arm could carry one or more samples. Also, in any particular arrangement there may be a plurality of such arms and in that event the various arms may be of the same or different length so as to serve the same circle or different circles of vials 2.

Any suitable means may be adopted for attaching samples to the cover member 8. In the arrangement shown the cover member 8 has a plurality of sample stations 9 which correspond in position and number to the underlying vials 2. That is, it is possible to have a respective sample located above each vial 2 for immersion therein. The sample retaining means at any station 9 may include, as shown, a rod 10 which depends from the undersurface of the cover member 8 and a cage or basket 11 attached to the lower end of the rod 10 and adapted to hold a tissue sample (not shown).

Preferably, the upper end of each rod 10 is secured to a cap 12 which is located within a hole formed through the cover member 8 and which is removable from that hole to enable a sample to be placed in or removed from the respective cage or basket 11. That is, the cap 12 is accessible at the top of the cover member 8 so that the attached sample retainer 10,11 can be lifted upwardly through the associated hole and thereby separated from the cover member 8.

Figure 1:
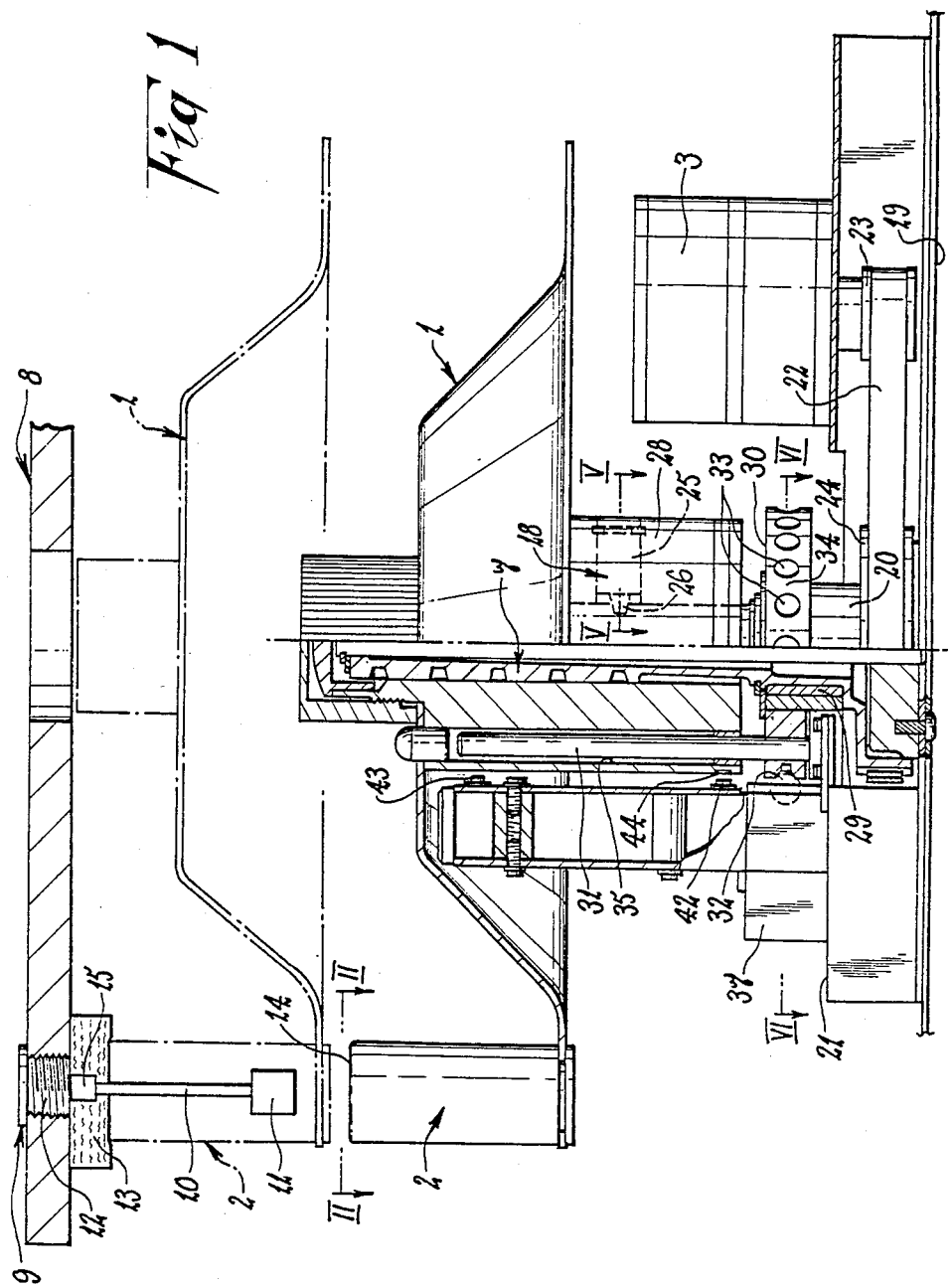
FIG. 1 is a semidiagrammatic view of one form of apparatus according to the invention.

Control mechanism is provided whereby the table 1 can be moved axially up and down to respectively position a sample within a vial 2 as shown in broken line in FIG. 1, and separate the vial 2 from the sample as shown in full line in FIG. 1. In an alternative arrangement which is not shown, the cover member 8 could be moved towards and away from the table 1 to achieve the same result, but the former arrangement is favoured in the apparatus herein described. An annular pad 13 of resilient material such as sponge rubber may be provided on the undersurface of the cover member 8 at each sample station 9 so as to be engagable against the rim surrounding the open mouth 14 of an underlying vial 2. That is, when the table 1 is raised to the sample immersion position as shown in broke line in FIG. 1 the rim of each vial 2 engages a respective pad 13 so that the open mouth 14 of the vial 2 is substantially sealed.

For the purpose of processing tissue samples, each vial 2 of the group carried by the table 1 may contain a different solution within which the sample is to be sequentially immersed. It is generally preferred to effect some agitation of the sample and/or the vial contents during the immersion so as to ensure that the solution will have maximum affect on the sample. That may be achieved through use of a piezo crytal 15 attached to each sample retainer rod 10 and arranged to be energized by appropriate means (not shown). The agitating means can take other forms however, and by way of example could be any suitable electrical, electrical/mechanical, or electro-magnetic device. In the example shown, each rod 10 is attached to its respective cap 12 through such a crystal 15.

Control mechanism for the table 1 includes the reversible drive motor 3 and transmission mean interconnecting the drive motor 3 and table 1. The motor 3 operates in either a forward mode or a reverse mode, and the transmission means is arranged so that it responds to one mode of operation to cause rotation of the table 1 and responds to the other mode to cause up and down movement of the table 1. In a typical sequence of operations, the table 1 is raised to the limit of its upward travel and held there for a suitable period of time, it is then lowered and rotated through a predetermined distance while in the lowered position to be conditioned for commencement of another sequence of operations.

Figure 4:
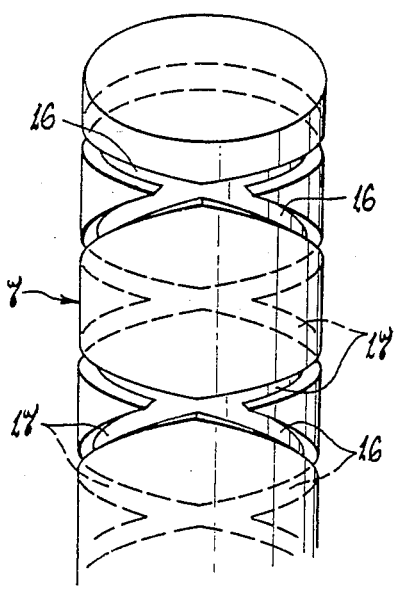
FIG. 4 is a diagrammatic view of part only of the central spindle of the apparatus shown in FIG. 1.

In the particular arrangement shown, the transmission means includes an upstanding spindle 7 having a two-way helix formed therein. That is, the helix includes two intersecting helical tracks 16 and 17 which extend along the spindle 7 at opposite angles as shown in FIG. 4. A follower 18 is arranged to engage with either helix track 16 or 17 and is attached to or forms part of the table 1. The spindle 7 forms the aforementioned support column for the table 1 and it is mounted for rotation relative to a support structure which may include or be attached to a base plate 19 of the apparatus. As shown, a lower portion 20 of the spindle 7 may project downwardly through a support plate 21 which is located above the base plate 19 and is rotatably connected to that support plate 21 through a suitable bearing. The drive motor 3 may be connected direct to the lower portion 20 of the spindle 7 in any suitable fashion, but the connection shown includes a belt 22 and cooperating pulleys 23 and 24 secured to the motor 3 and spindle 7 respectively.

Figure 5:
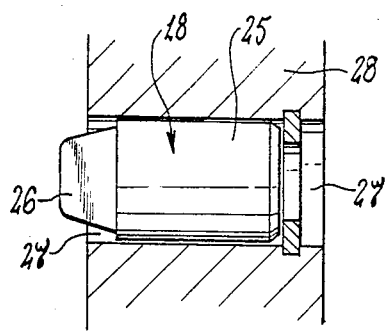
FIG. 5 is an enlarged cross sectional view taken along line V—V of FIG. 1.

As shown in FIG. 5, in the particular arrangement shown the follower 18 includes a cylindrical body 25 and a flat tongue portion 26 which projects from one end of the body 25. The body 25 is located within a bore 27 of a sleeve 28 which is secured to the table 1 so as to rotate with that table 1 and the tongue portion 26 projects out of the sleeve 28 as shown in FIG. 1 so as to locate within either of the helical tracks 16 and 17. The arrangement is such that the follower body 25 can rotate about its longitudinal axis relative to the sleeve 28 and thereby allow the tongue portion 26 to adapt itself to the slope of the particular track 16 or 17 within which it locates.

The transmission means also includes a drive connection between the motor 3 and the table 1 which includes a one-way clutch 29 (e.g., a sprag clutch) so that the table 1 is caused to rotate when the motor 3 is turning in one particular direction. In the particular arrangement shown, that drive connection includes a drive plate 30 which forms part of the rotatable mounting of the spindle 7 on the support plate 21. That is, the drive plate 30 is connected to the support plate 21 through the aforementioned bearing and the one-way clutch 29 is located between the drive plate 30 and the spindle 7. A thrust bearing may be provided between the spindle 7 and the drive plate 30 to facilitate relative rotation of those components and take the downward load of the spindle 7.

Drive means is provided between the drive plate 30 and the table 1 whereby rotary motion of the drive plate 30 is transmitted to the table 1. That drive means may be releasable as a consequence of axial movement of the table 1 relative to the drive plate 30, but in the arrangement shown it remains effective at all axial positions of the table 1. In the arrangement shown, the drive means includes a coupling, part of which is formed by a rod 31 secured to the drive plate 30 at a location radially outwards of the spindle 7 and extending upwardly from the drive plate 30 in a direction of the spindle axis. The rod 31 slidably locates within a passage 35 provided in the table sleeve 28 so that the sleeve 28 moves along the rod 31 during travel of the table 1 up and down the spindle 7. It is to be appreciated that the apparatus could include two or more rods 31 rather than one as shown.

It is preferred that the motor 3 is a pulse operated stepper motor and that operation of the motor 3 is controlled through suitable circuitry which may, for example, form part of a micro-processor. The control circuitry will be arranged to determine the desired sequence of operations and the time delay at various stages of that sequence. It may also includes a monitoring function to ensure that certain operations are completed before the apparatus is directed to perform subsequent stages.

Assuming the table 3 is in the lowered position, it may be releasably retained in a particular rotational position by detent means . As shown, a spring loaded detent ball 32 may be used for that purpose and that ball 32 is carried by the support structure and arranged to locate in any of a plurality of indexing recesses 33 formed in a cylindrical surface 34 of the drive plate 30. It is possible to use locators having a form different to that of the recesses 33 as shown. For example, they could be in the form of peripheral slots. The number of recesses 33 and their spacing will be selected to suit the number and location of the sample processing stations of the apparatus. By way of example, there may be twenty stations located at regularly spaced intervals. That is, at each rotational position of the table 1 as determined by the detent ball 32, a vial 2 carried by that table 1 is located directly beneath a particular sample station 9 of the cover member 8.

It is preferred to provide means for positively restraining the detent ball 32 against disengagement from an indexing recess 33 while the table 1 is being moved between its raised and lowered positions, or while sample procesing is actually taking place. One manner of achieving that retention is shown by FIGS. 6 and 7 and in that particular arrangement a solenoid 36 is operative to positively prevent withdrawal of the detent ball 32 from the recess engaging position as shown by FIG. 6.

Figure 6:
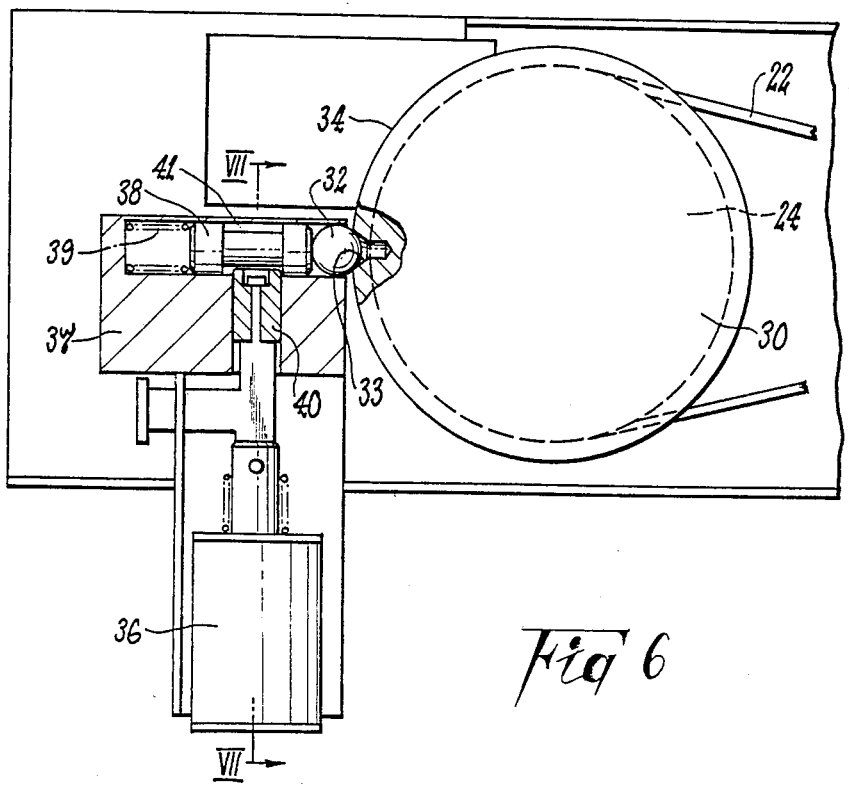
FIG. 6 is an enlarged cross sectional view taken along line VI—VI of FIG. 1.
Figure 7:
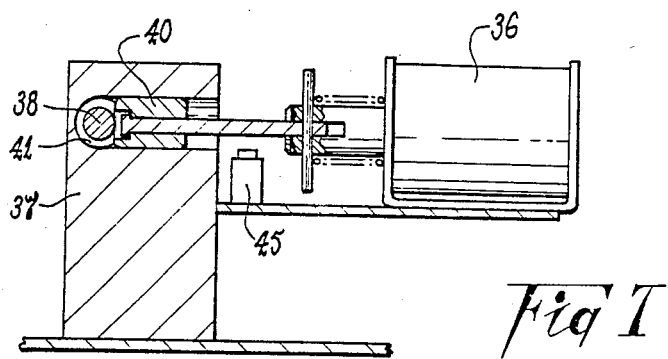
FIG. 7 is a cross sectional view taken along line VII—VII of FIG. 6.

In the FIGS. 6 and 7 arrangement the detent ball 32 is urged outwards of its mounting 37 by means of a plunger 38 and associated spring 39. The solenoid 36 is operative to drive a locking member 40 into a circumferential recess 41 provided around the plunger 38 and thereby prevent disengagement of the detent ball 32 from a recess 33. In the arrangement shown the solenoid 36 is spring biased into that locking condition and when the solenoid 36 is energized it operates to withdraw the member 40 from the detent locking position and thereby permit disengaging movement of the detent ball 32.

The solenoid 36 can be connected into the control circuitry of the apparatus so as to lock and free the detent ball 32 at appropriate times within an operating sequence. Operator sensor means 45 is responsive to movement of the solenoid 36 so as to provide an indication of whether or not the solenoid 36 is operable to lock or release the detent. Obviously, other means could be adopted for the purpose of detecting the solenoid condition.

If the drive motor 3 is energized to rotate the spindle 7 in the clutch release direction, the follower 18 will be caused to move along say the helix track 16 and thereby lift the table 1. In that regard, the drive plate 30 is restrained against rotation by the detent ball 32 and consequently the table is also held against rotation as it moves axially up the spindle 7. Operation of the motor 3 ceases when the table 1 reaches the liimt of its upward travel and at that time the sample at a particular station 9 is located within a respective vial 2. in that regard, limit switches which form part of the motor control may be arranged for operation at the extremities of the axial travel of the table 1.

In the arrangement shown optical sensors 42 and 43 (FIG. 1) detect when the table 1 is in its fully lowered and fully raised positions respectively. For that purpose the sensors 42 and 43 may respond to a mark 44 provided on the sleeve 28. Another optical sensor (not shown) may function to monitor the rotational positions of the table 1.

More than one sample may be provided in the retaining means 11 at one or more of the stations 9, but it will be convenient to refer to one sample only for the purpose of the present description. Each vial 2 contains an appropriate and respective solution for the purpose of processing the immersed sample, and a different period of immersion may be required for some of the solutions and/or samples. The control circuitry can be arranged to automatically attend to such differences. During the immersion, the piezo crystals 15 are energized so as to produce suitable agitation of the associated samples.

At the end of the immersion period the control circuitry operates to again turn the motor 3 in the clutch release direction. Since the follower 18 is at the top of its travel it is caused to transfer to the other helix track 17 which then influences the follower 18, and consequently the table 1, to move downwards. Rotation of the motor 3 in the aforementioned direction ceases when the table 1 reaches its lowermost position as permitted by the cooperating follower 18 and helix track 17.

Assuming the apparatus is only part way through the processing of a sample, it will be necessary to rotate the table 1 while in the lowered position in order to place each vial 2 beneath a different sample station 9. The control circuitry therefore causes the motor 3 to turn in the clutch engaged direction so that the drive plate 30 will follow rotation of the spindle 7. The driving force applied to the drive plate 30 by the spindle 7 overcomes the resistance of the detent spring 39 so that the ball 32 is cammed out of the recess 33 in which it was engaged. The detent ball 32 then tracks around the cylindrical surface 34 of the drive plate 30 and locates in another recess to index the table 1 into its next sample station position, at which time operation of the drive motor 3 ceases.

When the table 1 has been indexed as described the control circuitry commences to set in motion another sequence of operations as also described above.

It will be apparent from the foregoing description that the present invention provides a relatively simple yet effective apparatus for processing samples. The use of a single motor to perform several functions is of particular advantage.

In a typical arrangement, there will be one example retainer 11 only attached to the cover member 8 and that will hold one or more samples to be immersed sequentially in each of the vials 2. In that regard, the table 1 may carry the maximum number of vials 2 allowed by the construction of that table 1 or it may carry a lesser number of such vials 2 according to the requirements for the particular sample being processed. Assuming a single circular row of sample stations 9 is provided, there may be a plurality of sample retainers 11 in that row located at suitably spaced intervals and each such interval will bridge a number of stations 9 equivalent to the maximum number of vials 2 in which a particular sample is to be immersed. If there is more than one row of stations 9, each row may include one or more sample retainers 11, according to the requirements.

In a variation of the arrangement particularly described the sample may be mounted on the table 1 and solutions for receiving those samples could be mounted in any appropriate fashion relative to the table 1. By way of example, mechanism may be operable to present each of several solutions in turn to a particular sample while the table is stationary, and the table is then rotated to allow processing of a further sample in the same manner.

Various alterations, modifications and/or additions may be introduced into the constructions and arrangements of parts previously described without departing from the spirit or ambit of the invention as defined by the appended claims.

Having now described my invention what I claim as new and desire to secure by Letters Patent is:

1. Sample processing apparatus including, a carousel mounted for rotation and for back and forth movement in the direction of the axis of said rotation, said carousel being in the form of a table which is adapted to carry a plurality of containers, a sample supporting member overlying said carousel and arranged to carry at least one sample so that the sample may be immersed in a said container when the carousel is in a raised position, and control mechanism operable to cause said rotation and said axial movement of the carousel, said control mechanism including, a drive motor which operates both in a forward mode and a reverse mode and transmission means which interconnects said carousel and said drive motor, said transmission means being responsive to operation of said motor in one said mode to cause said carousel rotation and being responsive to operation of said motor in the other said mode to cause said carousel axial movement.

2. Apparatus according to claim 1, wherein the sample supporting member is in the form of a plate-like cover which is restrained against movement with said table.

3. Apparatus according to claim 1, wherein optical sensor means is operable to detect both the rotational and axial positions of said carousel.

4. Apparatus according to claim 1, wherein agitating means is operable to cause movement of a said sample while immersed in a said container.

5. Sample processing apparatus including, a carousel for carrying at least one of a sample and a container in which a sampale is immersible, said carousel mounted for rotation and for back forth movement in the direction of the axis of said rotation, an upstanding rotatable spindle having a two-way helix formed therealong, said carousel being mounted on said spindle, a follower connected to said carousel and engaging with said helix so as to cooperate therewith and thereby cause said axial movement of the carousel, and control mechanism operable to cause said rotation and said axial movement of the carousel, said control mechanism including, a drive motor which operates both in a forward mode and reverse mode and transmission means which interconnects said carousel and said drive motor, said transmission means being responsive to operation of said motor in one said mode to cause said carousel rotation and being responsive to operation of said motor in the other said mode to cause said carousel axial movement.

6. Apparatus according to claim 5, wherein retention means is operative to restrain said carousel against rotation with said spindle when said motor is operating in said other mode.

7. Apparatus according to claim 5, wherein said transmission means includes a drive connection between said motor and said carousel, and said drive connection includes said spindle and a one-way clutch between said spindle and said carousel and which operates to allow said spindle to rotate relative to said carousel in one direction and to prevent said relative rotation in the opposite direction.

8. Apparatus according to claim 7, wherein said drive connection includes a drive plate and coupling means interconnecting said drive plate and said carousel so as to prevent relative rotation of said drive plate and carousel but permit relative axial movement thereof, said one-way clutch acts between said spindle and said drive plate, and said spindle rotates in response to operation of said motor in either said mode thereof.

9. Apparatus according to claim 8, wherein said coupling means includes a rod secured to said drive plate at a location radially outwards of said spindle and extending substantially in the axial direction of the spindle, and said slidably engages with said carousel.

10. Apparatus according to claim 8, wherein retention means is operative to restrain said drive plate against rotation with said spindle when said motor is operating in said other mode.

11. Apparatus according to claim 10, wherein said retention means includes a spring loaded detent which is engagable with any one of a plurality of indexing locators provided around said drive plate.

12. Apparatus according to claim 11, wherein a solenoid is operable to retain said detent against disengagement from a said locator.

13. Apparatus according to claim 12, wherein sensor means is operable to determine whether said solenoid is operable or inoperable.

* * * * *